United States Patent
Bonne et al.

(10) Patent No.: US 6,393,894 B1
(45) Date of Patent: May 28, 2002

(54) GAS SENSOR WITH PHASED HEATERS FOR INCREASED SENSITIVITY

(75) Inventors: Ulrich Bonne; Jay Goetz, both of Hennepin County, MN (US); Purnendu K. Dasgupta, Lubbock County, TX (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/361,886

(22) Filed: Jul. 27, 1999

(51) Int. Cl.[7] ............................................. G01N 30/00
(52) U.S. Cl. ..................... 73/23.2; 73/31.07; 422/88
(58) Field of Search ............................. 73/23.2, 31.07; 422/88

(56) References Cited

U.S. PATENT DOCUMENTS

| | | |
|---|---|---|
| 3,146,616 A | 9/1964 | Loyd ........................ 73/23.26 |
| 3,557,532 A | 1/1971 | Broerman ...................... 95/87 |
| 3,783,356 A | 1/1974 | Lide, III et al. |
| 4,043,196 A | 8/1977 | Trageser |
| 4,228,815 A | 10/1980 | Juffa et al. |
| 4,478,076 A | 10/1984 | Bohrer |
| 4,483,200 A | 11/1984 | Togawa et al. |
| 4,507,974 A | 4/1985 | Yelderman |
| 4,576,050 A | 3/1986 | Lambert |
| 4,735,082 A | 4/1988 | Kolloff |

(List continued on next page.)

FOREIGN PATENT DOCUMENTS

| | | |
|---|---|---|
| DE | 2 934 566 A1 | 3/1981 |
| DE | 32 34 146 A1 | 3/1984 |
| DE | 42 22 458 A1 | 1/1994 |
| DE | 42 43 573 A1 | 6/1994 |
| DE | 296 07 315 U1 | 9/1996 |
| DE | 196 19 133 A1 | 11/1997 |
| EP | 0 232 719 A1 | 1/1987 |
| EP | 0 348 245 A2 | 12/1989 |
| EP | 0 364 982 A2 | 4/1990 |
| EP | 0 419 873 A2 | 8/1990 |

(List continued on next page.)

OTHER PUBLICATIONS

S.R. Atalla et al. "Measurement of Thermal Properties of Liquids with an AC Heated–Wire Technique", *International Journal of Thermophysics*, vol. 2, No. 2, 1981.

Sobhy R. Atalla et al., "Radiation Effects with the AC Heated Strip Technique for the Measurement of Thermal Properties of Liquids", *High Temperatures–High Pressures*, vol. 17, pp. 447–452, 1985.

"Quartz Crystal Gas Monitor With Gas Concentrating Stage", Kindlund et al., Sensors and Actuators, 6 (1984) pp. 1–17.

(List continued on next page.)

*Primary Examiner*—Daniel S. Larkin
(74) *Attorney, Agent, or Firm*—Kris T. Fredrick (57) ABSTRACT

A concentrator and sensor assembly are disclosed that use phased heaters to multiply the concentration levels that can be eluted, relative to operation with a single interactive element having a sorbent material to increase the concentration of desired gas constituents at a detector. This is accomplished here by providing two or more interactive concentrator elements that are selectively heated in a time phased sequence so that each of the interactive elements becomes heated and desorbs gas constituents into the sample fluid stream at substantially the same time that an upstream concentration pulse, produced by heating one or more upstream interactive elements, reaches the interactive element. This produces a multiplication effect that significantly increases the concentration of the gas constituents at the detector, thereby increasing the effective sensitivity of the detector.

29 Claims, 9 Drawing Sheets

U.S. PATENT DOCUMENTS

| | | | |
|---|---|---|---|
| 4,759,210 A | 7/1988 | Wohltjen | 73/23.2 |
| 4,909,078 A | 3/1990 | Sittler et al. | |
| 4,944,035 A | 7/1990 | Aagardl et al. | |
| 5,031,126 A | 7/1991 | McCulloch et al. | |
| 5,044,766 A | 9/1991 | Stuart | |
| 5,056,047 A | 10/1991 | Sondergeld | |
| 5,146,414 A | 9/1992 | McKown et al. | |
| 5,243,858 A | 9/1993 | Erskine et al. | |
| 5,263,380 A | 11/1993 | Sultan et al. | |
| 5,268,302 A | 12/1993 | Rounbehler et al. | 436/96 |
| 5,379,630 A | 1/1995 | Lacey | |
| 5,463,899 A | 11/1995 | Zemel et al. | |
| 5,533,412 A | 7/1996 | Jerman et al. | |
| 5,587,520 A | 12/1996 | Rhodes | |
| 5,922,974 A | 7/1999 | Davidson et al. | |
| 5,985,673 A * | 11/1999 | Bao et al. | 73/23.2 X |

FOREIGN PATENT DOCUMENTS

| | | |
|---|---|---|
| EP | 0 468 793 A2 | 1/1992 |
| EP | 0 702 212 A2 | 3/1996 |
| EP | 0 773 432 A2 | 5/1997 |
| GB | 2 287 792 A | 9/1995 |
| JP | 56-153256 | 11/1981 |
| JP | 57-131029 | 8/1982 |
| JP | 57-206830 | 12/1982 |
| WO | WO 92/06369 | 4/1992 |
| WO | WO 94/20825 | 9/1994 |
| WO | 22793 | 5/1998 |

OTHER PUBLICATIONS

"Design and development of a fiber optic TDI CCD–based slot–scan digital mammography system", Toker et al., X–ray Dector Physics and Applications II, Proceedings SPIE—The International Society for Optical Engineering, vol. 2009 (Jul. 13–14, 1993) pp. 246–252.

"Double–Injection FIA Using First–Order Calibration for Multicomponent Analysis", D.A. Whitman et al., Analytical Chemistry 63 (1991) p. 775.

Endre Fuggerth, "Zone Gas Chromatography", 266b Analytical Chemistry, 61 (1989) Jul. 15, No. 14, Washington, D.C., USA, pp. 1478–1485.

* cited by examiner

GAS SENSOR WITH PHASED HEATERS FOR INCREASED SENSITIVITY

BACKGROUND OF THE INVENTION

The present invention relates to gas monitoring devices, and more particularly to methods and apparatus for detecting and identifying various gas constituents in a sample gas stream and/or determining the concentrations of such constituents.

The detection of gases and vapors at low concentrations is often difficult due to limitations in the sensitivity of detector devices and measurement instruments. The process of detecting various constituents within a gas sample at low concentrations can be greatly enhanced if the constituents can be concentrated prior to detection. One approach for concentrating selected constituent gases is described in "Quartz Crystal Gas Monitor With Gas Concentrating Stage", Kindlund et al, Sensors and Actuators, 6 (1984) pp. 1–17. Kindlund et al. suggest providing a gas concentrator in front of a detector to increase the concentration of the desired gas constituents at the detector. The gas concentrator of Kindlund et al. includes a thick organic sorbent layer that is coated on the walls of a cavity. When cool, the sorbent layer adsorbs the desired gas constituents from the gas sample flowing through the cavity. A heating pulse is then applied to the sorbent layer, causing the adsorbed constituents to desorbs into the cavity to produce a short concentration pulse. The concentration pulse is conducted to a quartz crystal gas monitor that ultimately registers the presence of the constituent.

A limitation of Kindlund et al. is that typically sorbent materials can only accumulate a limited amount of gas constituents. Thus, the concentration pulse produced when the sorbent layer is heated is also limited, thereby limiting the effective sensitivity of the detector. What would be desirable, therefore, is a concentrator and/or sensor assembly that can further increase the concentration level of desired gas constituents at the detector to produce a detector of increased effective sensitivity.

SUMMARY OF THE INVENTION

The present invention overcomes many of the disadvantages associated with the prior art by providing a concentrator and sensor assembly that use phased heaters to increase or multiply the concentration levels beyond those that can be achieved by a single interactive element having a sorbent material. Generally, this is accomplished by providing two or more interactive elements that are selectively heated in a time phased sequence so that each of the interactive elements becomes heated and desorbs constituent gases into the sample fluid stream at substantially the time that an upstream concentration pulse, produced by heating one or more upstream interactive elements, reaches the interactive element. As can be seen, this produces a multiplication effect that can significantly increase the concentration of the gas constituents at the detector, thereby increasing the effective sensitivity of the detector.

In a first illustrative embodiment, a concentrator is provided for concentrating one or more constituents in a sample fluid stream. The concentrator preferably has two or more interactive elements spaced along and exposed to the sample fluid stream. Each of the interactive elements include an interactive substance that adsorbs and desorbs selected constituents of the sample fluid stream, depending on the temperature of the interactive element. Two or more heater elements are provided, with each heater element in thermal communication with a corresponding interactive element.

A controller energizes the heater elements in a time phased sequence. The controller preferably energizes the heater elements such that each of the corresponding interactive elements become heated and desorb selected constituents into the sample fluid stream at substantially the time at which an upstream concentration pulse, produced by one or more upstream interactive elements, reaches the interactive element. It is contemplated that a large number, N, of interactive elements may be used to achieve the desired multiplication of concentration of constituent gases in the concentration pulse by a factor N.

The resulting concentration pulse may then be provided directly to a detector for detection and analysis. The detector may be a thermal conductivity detector, discharge ionization detector, or any other type of detector such as those commonly used in gas chromatography. More preferably, however, the resulting concentration pulse is first provided to a separator. The separator separates selected gas constituents of the resulting concentration pulse into individual constituent components. The detector may then detect the concentration of each constituent that elutes from the separator.

The heater elements are preferably formed from a resistive material having a common resistance and length along the flow direction. As such, the controller can equally energize the heater elements by providing an equal voltage, current, or power pulse to each heater element. The voltage, current, or power pulse may have any desired shape including a triangular shape, a square shape, a bell shape, or any other shape. The shape or height of the voltage, current, or power pulse may even be chosen to produce a temperature profile that only desorbs selected gas constituents from the sorbent material.

It is also contemplated that the length of the heater elements may increase along the sample fluid stream. The length of each heater element may be increased, relative to the upstream heater elements, by an amount that corresponds to the expected increased length of the concentration pulse of the upstream heater elements caused by diffusion. To match this diffusion effect for best utilization of the growing concentration wave in the concentrator, the length of each of the heater elements may be similarly increased to produce the same resistance, thereby tailoring equal voltage, current, or power pulses to be used for each heater element to achieve equal temperature profiles. Alternatively, all heater elements may have the same length as the N-th element, so that the controller may provide equal voltage, current, or power pulses, suitably phased in time, to all heater elements to result in equal temperature profiles.

It is also contemplated that the two or more interactive elements need not be separate elements, but rather may be formed from a single interactive layer. Two or more heater elements may then be in thermal communication with different portions of the interactive layer. This configuration may simplify the manufacture of the concentrator.

The present invention also contemplated a number of methods. In one illustrative method, a sample fluid flow or stream is provided using a pump, thermal convection, or the like. The sample fluid stream is allowed to pass over two or more interactive elements (or an interactive layer) until the interactive elements adsorb one or more constituents from the sample fluid stream and reach equilibrium. Thereafter, the two or more interactive elements are heated in a time phased sequence.

Preferably, an upstream interactive element is first heated, which causes the upstream interactive element to increase in temperature and to desorb selected constituents into the sample fluid stream to produce a first concentration pulse that is carried by the sample fluid stream downstream toward a downstream interactive element. Thereafter, the downstream interactive element is heated as the first concentration pulse reaches the downstream interactive element. This causes the downstream interactive element to desorb selected constituents into the sample fluid stream and at least partially overlap the first concentration pulse to produce a larger concentration pulse that is carried by the sample fluid stream further downstream. The larger concentration pulse has an increased concentration level of the selected constituents than that of the first or second concentration pulses. It is contemplated that any number of downstream interactive elements may be heated in a like manner to produce an even further increased concentration level at the output of the concentrator.

After the concentrator provides a desired concentration pulse, selected constituents may be separated to provide one or more individual constituent components. The concentration of the individual constituent components may then be sensed and analyzed as desired.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
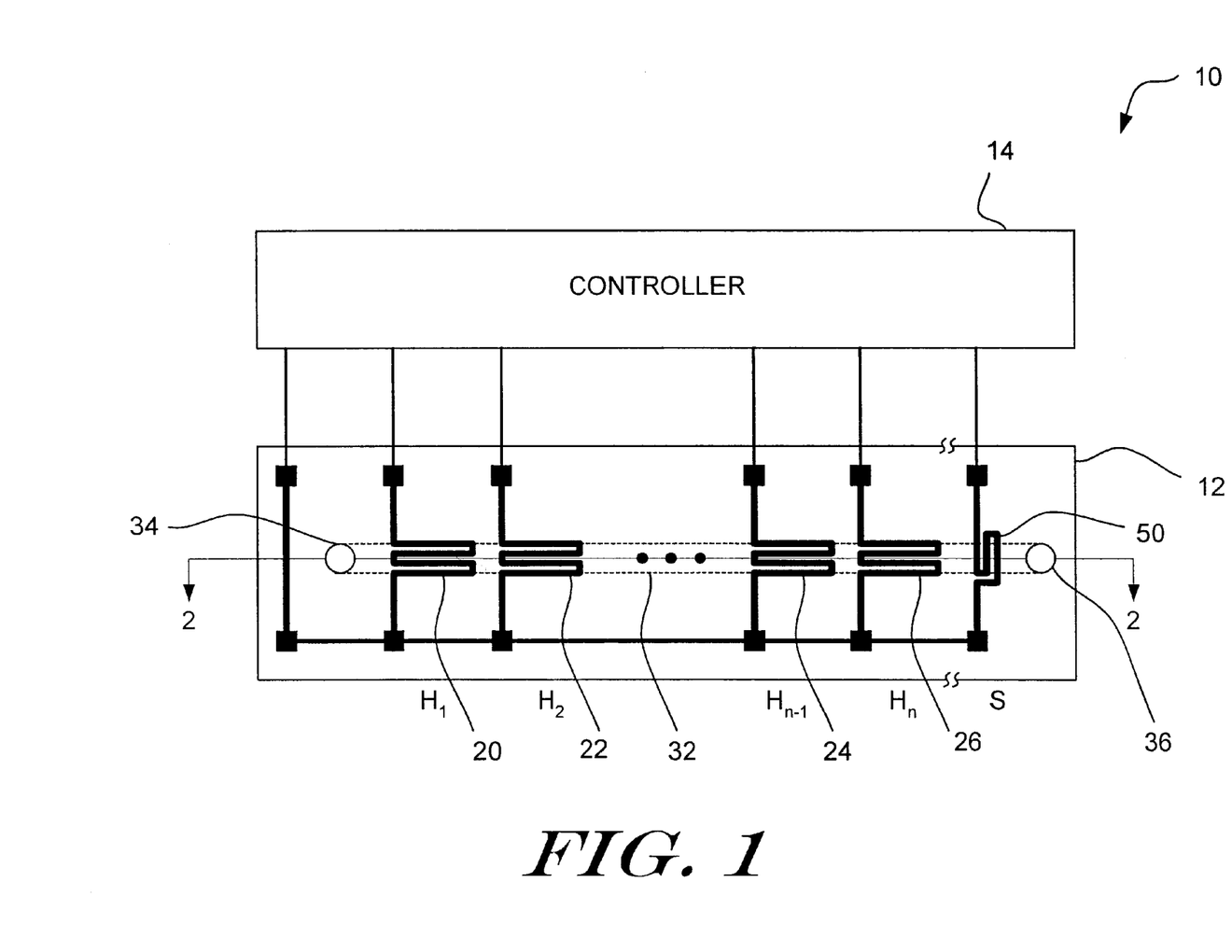
FIG. 1 is a schematic diagram of a first illustrative sensor apparatus according to the present invention.

FIG. 1 is a schematic diagram of a first illustrative sensor apparatus in accordance with the present invention. The sensor apparatus is generally shown at 10 and includes a substrate 12 and a controller 14. It is contemplated that the controller 14 may or may not be incorporated into substrate 12.

Figure 2:
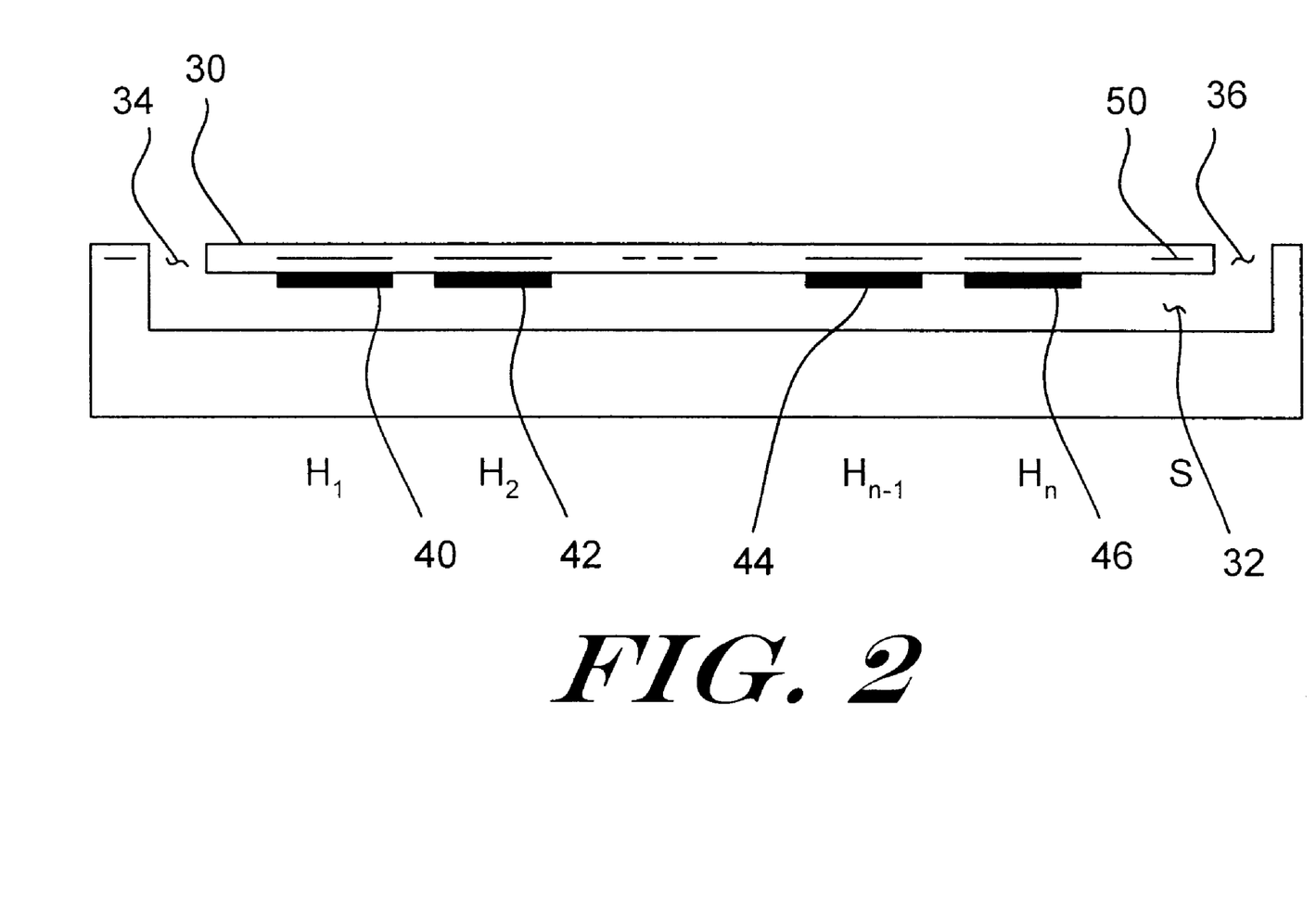
FIG. 2 is a cross-sectional view taken along line 2—2 of FIG. 1.

The substrate 12 preferably has a number of thin film heater elements 20, 22, 24, and 26 positioned thereon. While only four heater elements are shown, it is contemplated th at any number of heater e elements may be provided, preferably between one hundred and one thousand. Heater elements 20, 22, 24, and 26 may be fabricated of any suitable electrical conductor, stable metal, or alloy film, s such a s a nickel-iron alloy sometimes referred to as permalloy, with a composition of eighty percent nickel and twenty percent iron; platinum, platinum suicide, and polysilicon. The heater elements 20, 22, 24, and 26 are preferably provided on a thin, low-thermal mass, low-in-plane thermal conduction, support member 30, as best shown in FIG. 2.

The substrate 12 also preferably has an accurately defined channel 32 for receiving the sample fluid stream. The channel 32 is preferably fabricated by selectively etching the silicon substrate 12 beneath support member 30. The process of forming channel 32 may be similar to that used to form the microbridge system illustrated in U.S. Pat. No. 4,944,035 to Aagardl et al., which is incorporated herein by reference. The channel includes an entry port 34 and an exhaust port 36.

The sensor apparatus also preferably includes a number of interactive elements inside channel 32 so that they are exposed to the sample fluid stream. Each of the interactive elements is preferably positioned adjacent, i.e. closest possible contact, to a corresponding heater element. For example, and referring, to FIG. 2, interactive elements 40, 42, 44, and 46 are preferably provided on the lower surface of support m-ember 30, and adjacent to heater elements 20, 22, 24, and 26, respectively. The interactive elements may be formed from any number of films commonly used in liquid or gas chromatography, such as silica gel or active carbon.

In one embodiment, the interactive elements are formed by passing, a stream of material carrying the desired sorbent material through channel 32. This provides an interactive layer throughout the channel. If separate interactive elements are desired, the coating, may be selectively "developed" by providing a temperature change to the coating, via the heater elements. After the coating is developed, a stream of solvents may be provided through channel 32 to remove the coating everywhere except where the coating has been developed, leaving only the sorbent material that is adjacent the heater elements.

Controller 14 preferably is electrically connected to each of the heater elements 20, 22, 24, 26, and detector 50 as shown. The controller 14 energizes the heater elements 20, 22, 24, and 26 in a time phased sequence (see bottom of FIG. 3) such that each of the corresponding interactive elements 40, 42, 44, and 46 become heated and desorb selected constituents into the sample fluid stream at precisely the time when an upstream concentration pulse, produced by one or more upstream interactive elements, reaches the interactive element. It is contemplated that any number of interactive elements may be used to achieve the desired concentration of constituent gases in the concentration pulse. In the embodiment shown, the resulting concentration pulse is provided to detector 50 for detection and analysis. Detector 50 may be a thermal conductivity detector, discharge ionization detector, or any other type of detector such as those typically used in gas or fluid chromatography.

Figure 3:
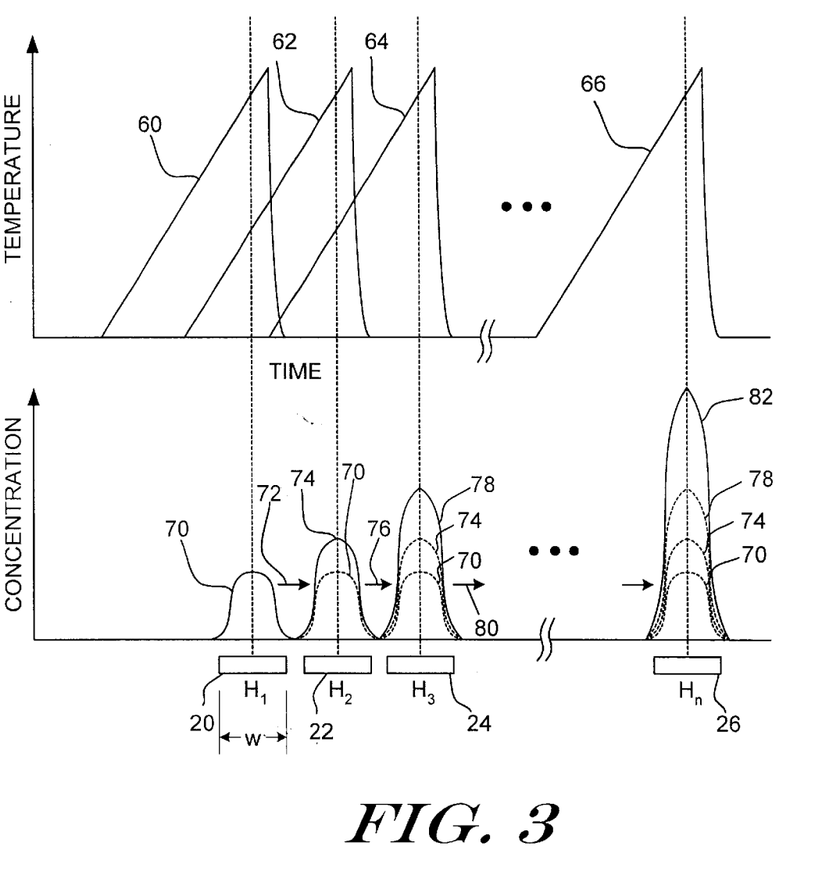
FIG. 3 is a graph showing illustrative heater temperatures, along with corresponding concentration pulses produced at each heater element.

FIG. 3 is a graph showing illustrative heater temperatures, along with corresponding concentration pulses produced at each heater element. As indicated above, the controller 14 may energize the heater elements 20, 22, 24, and 26 in a time phased sequence. Illustrative time phased heater temperatures for heater elements 20, 22, 24, and 26 are shown at 60, 62, 64, and 66, respectively.

In the example shown, the controller 14 (see FIG. 1) first energizes the first heater element 20 to increase its temperature as shown at 60. Since the first heater element 20 is thermally coupled to the first interactive element 40, the first interactive element desorbs selected constituents into the sample fluid stream to produce a first concentration pulse 70. The sample fluid stream carries the first concentration pulse 70 downstream toward the second heater element 22, as shown by arrow 72.

The controller 14 next energizes the second heater element 22 to increase its temperature as shown at 62. Since the second heater element 22 is thermally coupled to the second interactive element 42, the second interactive element also desorbs selected constituents into the sample fluid stream to produce a second concentration pulse. The controller 14 energizes the second heater element 22 such that the second concentration pulse substantially overlaps the first concentration pulse 70 to produce a higher concentration pulse 74, as shown. The sample fluid stream carries the larger concentration pulse 74 downstream toward the third heater element 24, as shown by arrow 76.

The controller 14 then energizes the third heater element 24 to increase its temperature as shown at 64. Since the third heater element 24 is thermally coupled to the third interactive element 44, the third interactive element 44 desorbs selected constituents into the sample fluid stream to produce a third concentration pulse. The controller 14 energizes the third heater element 24 such that the third concentration pulse substantially overlaps the larger concentration pulse 74 provided by the first and second heater elements 20 and 22 to produce an even larger concentration pulse 78, as shown. The sample fluid stream carries this larger concentration pulse 78 downstream toward the "Nth" heater element 26, as shown by arrow 80.

The controller 14 then energizes the "Nth" heater element 26 to increase its temperature as shown at 66. Since the "Nth" heater element 26 is thermally coupled to the "N-th" interactive element 46, the "N-th" interactive element 46 desorbs selected constituents into the sample fluid stream to produce an "N-th" concentration pulse. The controller 14 energizes the "N-th" heater element 26 such that the "N-th" concentration pulse substantially overlaps the larger concentration pulse 78 provided by the previous N-1 interactive elements, as shown. The sample fluid stream carries the "N-th" concentration pulse 82 to either a separator or a detector, as more fully described below.

As indicated above, the heater elements 20, 22, 24, and 26 may have a common length. As such, the controller can achieve equal temperatures of the heater elements by providing an equal voltage, current, or power pulse to each heater element. The voltage, current, or power pulse may have any desired shape including a triangular shape, a square shape, a bell shape, or any other shape. An approximately square shaped voltage, current, or power pulse is used to achieve the temperature profiles 60, 62, 64, and 66 shown in FIG. 3.

Figure 4:
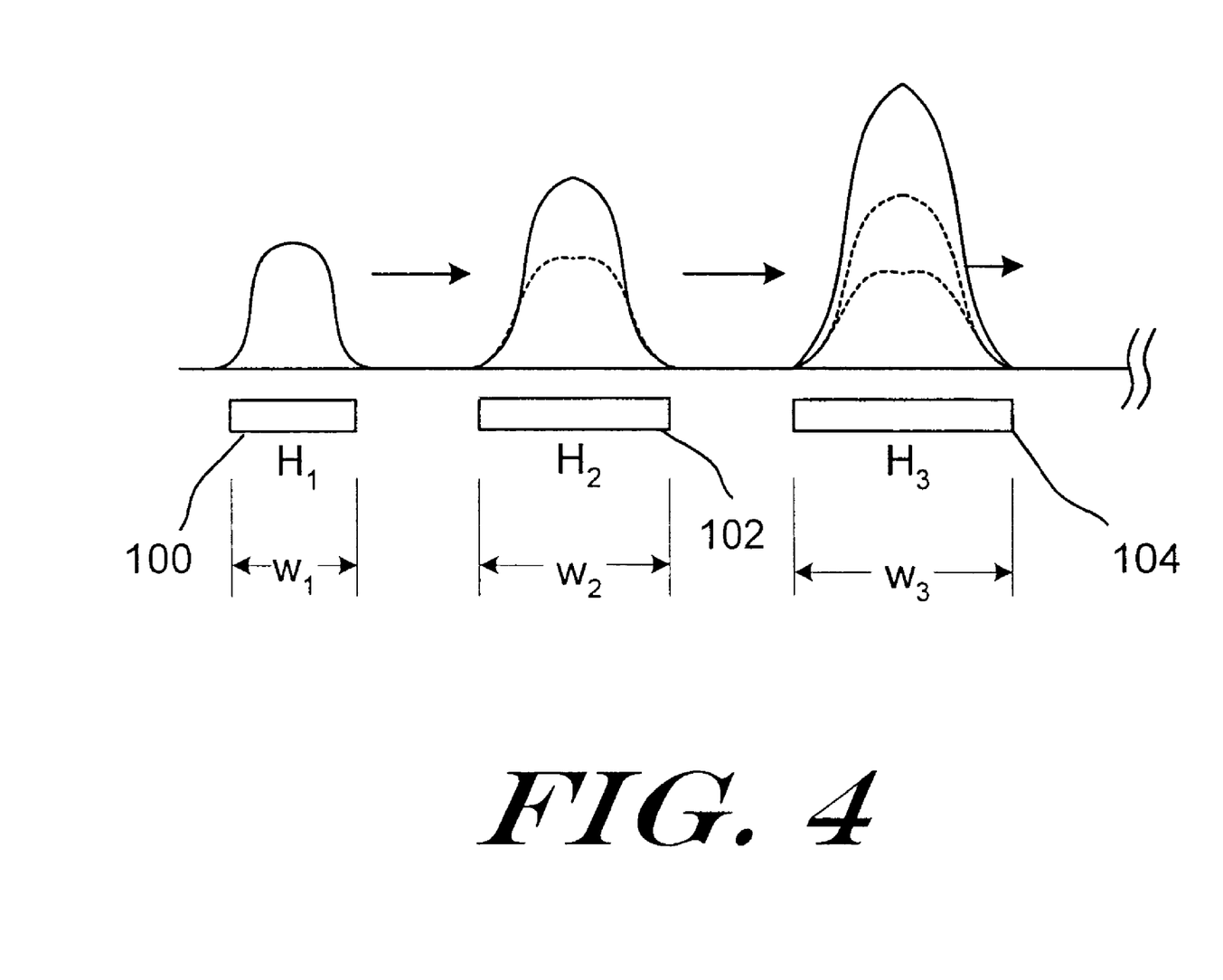
FIG. 4 is a graph showing a number of heater elements having lengths to match the expected increased lengths of the concentration pulses due to diffusion.

FIG. 4 is a graph showing a number of heater elements having lengths to match the expected increased length of the concentration pulses due to diffusion. It is recognized that each of the concentration pulses may tend to reduce in amplitude and increase in length when traveling down the channel 32 due to diffusion. To accommodate this increased length, it is contemplated that the length of each successive heater element may be increased along the sample fluid stream. For example, the second heater element 102 may have a length $W_2$ that is larger than the length $W_1$ of the first heater element 100. Likewise, the third heater element 104 may have a length $W_3$ that is larger than the length $W_2$ of the second heater element 102. Thus, it is contemplated that the length of each heater element 100, 102, and 104 may be increased, relative to the adjacent upstream heater element, by an amount that corresponds to the expected increased length of the concentration pulse of the upstream heater elements due to diffusion.

To simplify the control of the heater elements, the length of each successive heater element may be increased to produce the same overall heater resistance between heater elements, thereby allowing equal voltage, current, or power pulses to be used to produce similar temperature profiles. Alternatively, the heater elements may have different lengths, and the controller may provide different voltage, current, or power pulse amplitudes to the heater element to produce a similar temperature profile.

Figure 5:
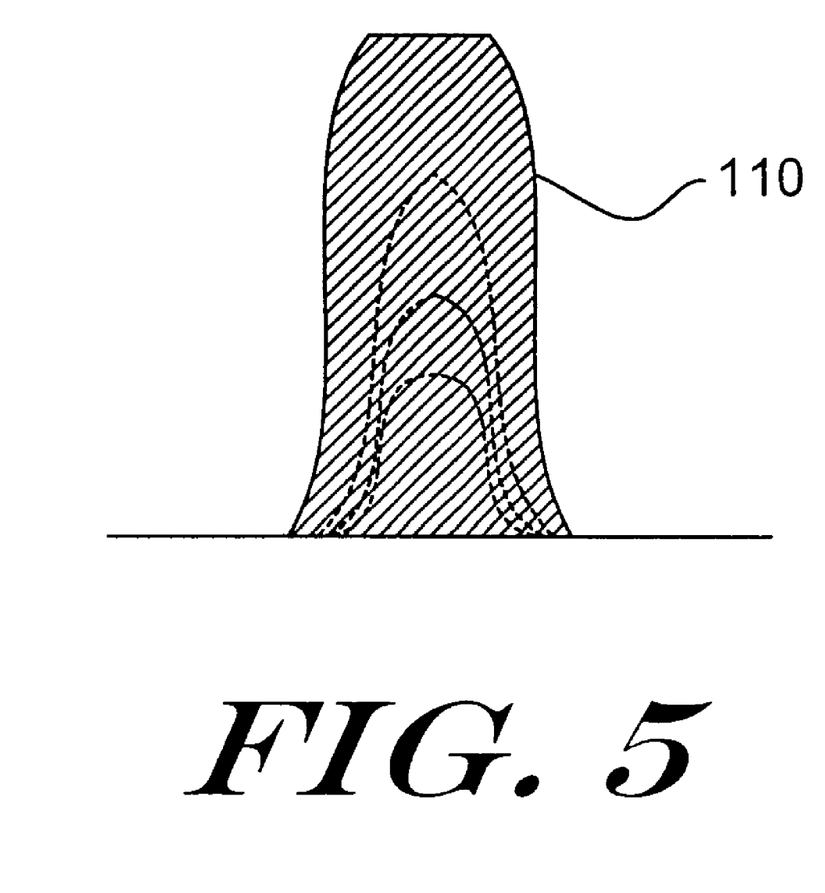
FIG. 5 is a graph showing a concentration pulse that reaches a 100% concentration level.

FIG. 5 is a graph showing a concentration pulse 110 that achieves a 100% concentration level. It is recognized that even though the concentration pulse 110 has achieved a predetermined concentration threshold, such as 100%, the concentration of the corresponding constituent can still be determined. To do so, the detector may detect the concentration pulse 110, and the controller 14 may integrate the output signal of the detector over time to determine the concentration of the corresponding constituent in the original sample.

Figure 6:
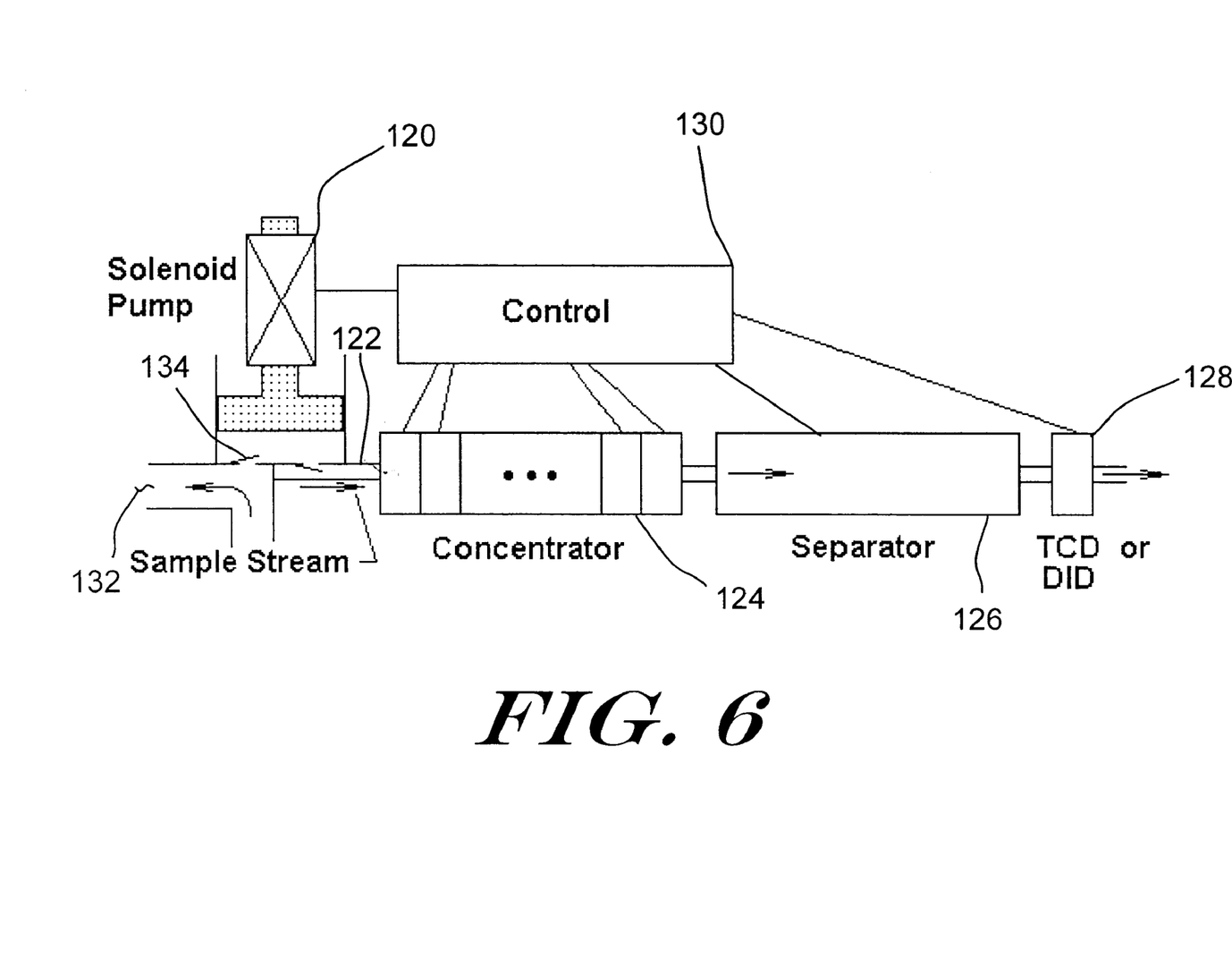
FIG. 6 is a schematic view of a sensor assembly in accordance with the present invention.

FIG. 6 is a schematic view of an illustrative sensor assembly in accordance with the present invention. The sensor assembly may include a solenoid pump 120, a sample fluid stream 122, a concentrator 124, a separator 126, a detector 128, and a controller 130. At the request of the controller 130, the solenoid pump 120 preferably draws a sample from a flue gas stream 132 through one way valve 134. The controller 130 may then direct the solenoid pump 120 to provide a sample fluid stream, at a desired pressure, to concentrator 124.

Concentrator 124 preferably includes two or more interactive elements that are in communication with the sample fluid stream. Concentrator 124 also preferably includes two or more heater elements that are in thermal communication with the interactive elements. When energized, each heater element heats a corresponding interactive element, causing the interactive element to desorb selected constituents into the sample fluid stream. As described above, controller 130 preferably energizes the heater elements in a time phased sequence to provide an increased concentration pulse.

The sample fluid stream carries the concentration pulse to separator 126. Separator 126 separates selected constituents of the concentration pulse and provides the separated constituents to detector 128. Detector 128 provides a signal to the controller 130 indicating the concentration level of each constituent. The controller 130 may determine the actual concentration level of each constituent in the original gas sample by dividing the sensed concentration level by the concentration amplification provided by the sorbent material of each interactive element and the multiplier effect provided by the phased heater arrangement.

Figure 7:
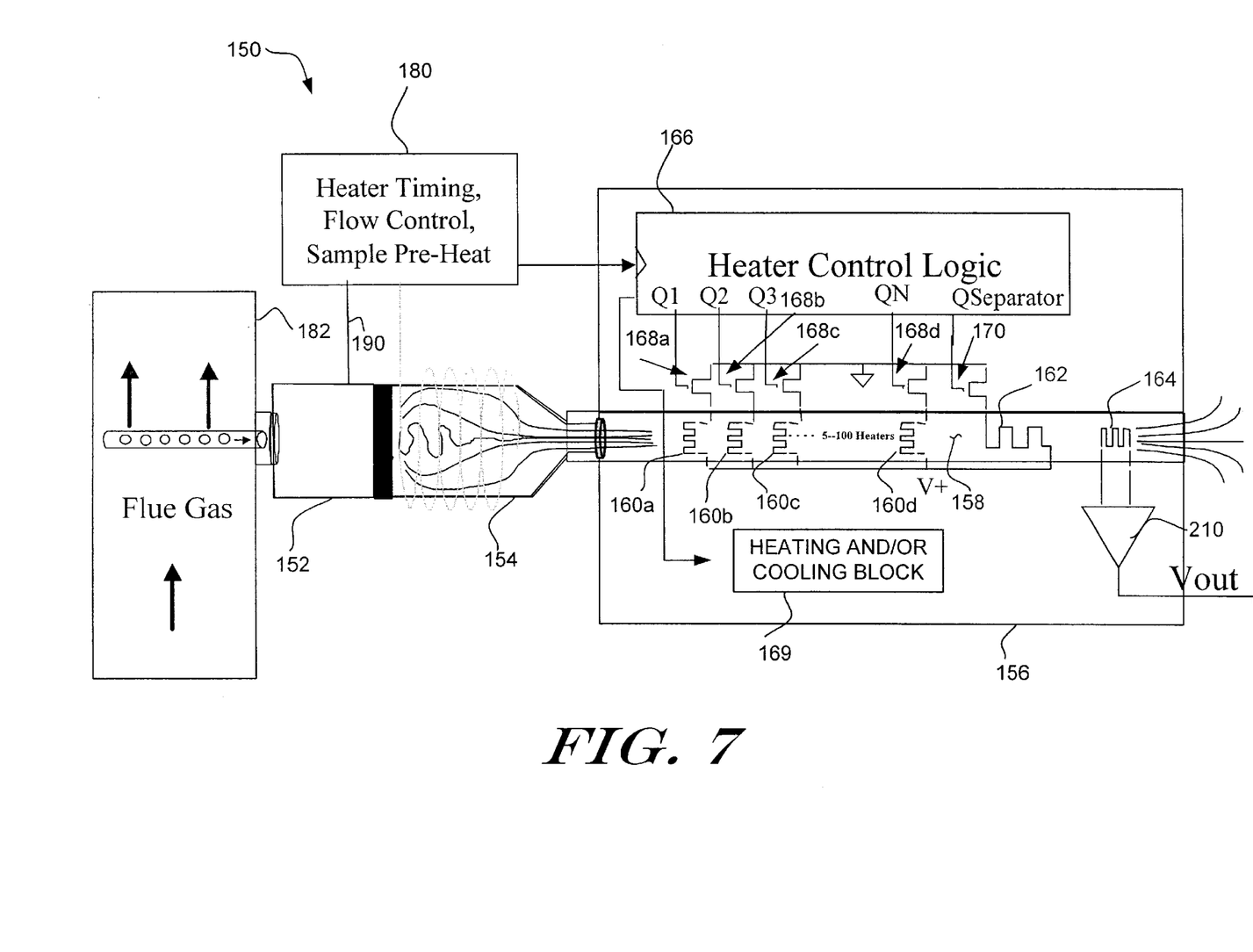
FIG. 7 is a schematic view of another sensor assembly in accordance with the present invention.
Figure 8:
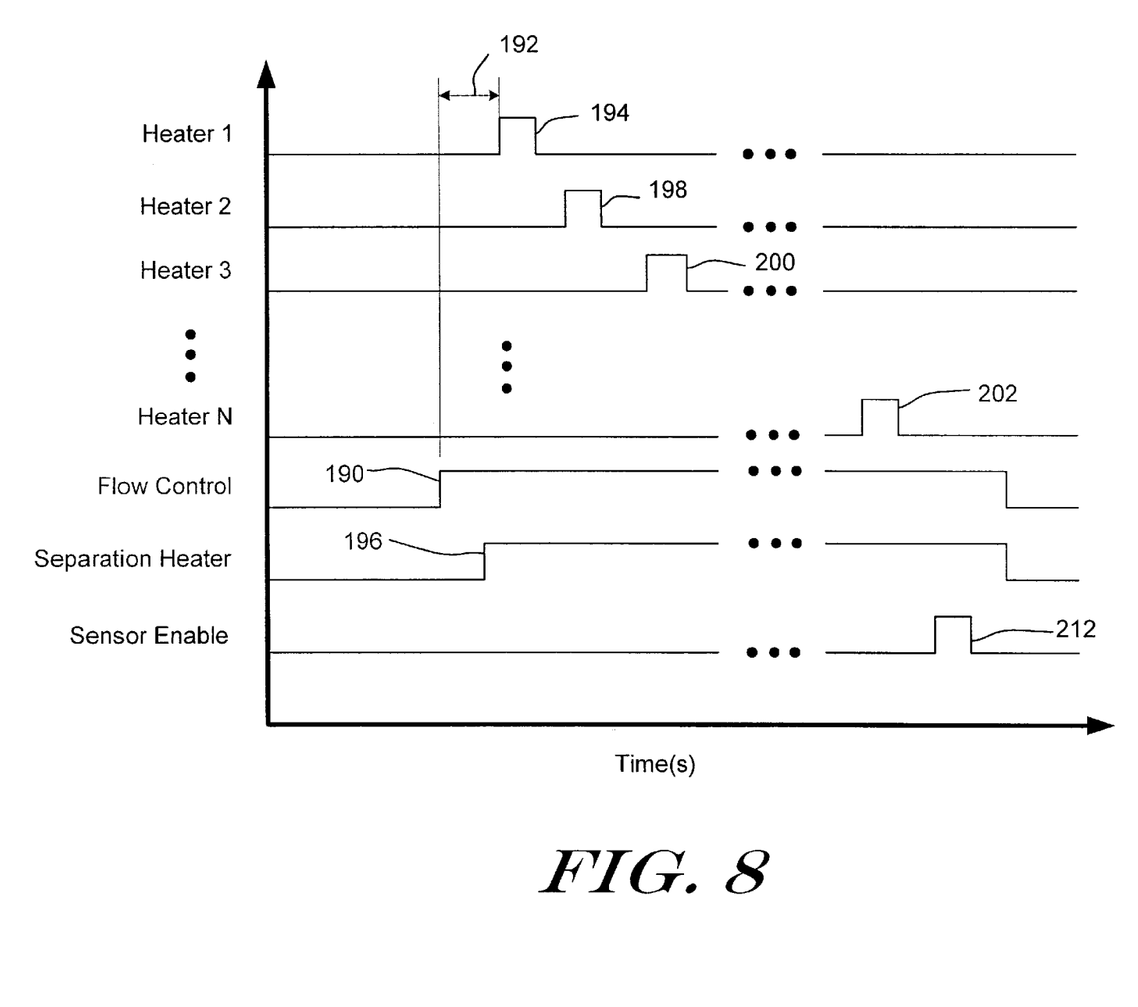
FIG. 8 is a timing chart showing the operation of the sensor assembly of FIG. 7.

FIG. 7 is a schematic view of another illustrative sensor assembly in accordance with the present invention. FIG. 8 is a timing chart showing the operation of the sensor assembly of FIG. 7. The sensor assembly is generally shown at 150, and may include a pump 152, a gas preheater 154, and a microbridge type integrated circuit chip 156. The microbridge type integrated circuit includes a channel 158, a number of heater elements 160a, 160b, 160c, and 160d, a separation heater 162, and a detector 164. Each of the heater elements 160a, 160b, 160c, and 160d, the separation heater 162, and the detector 164 are preferably provided on a support member that extends over the channel 158 (e.g. see FIG. 2). Interactive elements (not explicitly shown) are placed in the channel 158 and in thermal communication with each of the heater elements 160a, 160b, 160c, and 160d.

The microbridge type integrated circuit chip 156 also preferably includes a heater control block 166 and a number of energizing transistors 168a, 168b, 168c, 168d, and 170. The heater control block 166 can individually energize each of the heater elements 160a, 160b, 160c, and 160d, by activating the corresponding energizing transistor 168a, 168b, 168c, 168d. Likewise, the heater control block 166 can energize the separation heater 162 by turning on transistor 170. Heating or cooling block 169 (FIG. 7) complements preheater 154 in maintaining an average or overall temperature that is optimal for operation of the sensor assembly.

A sensor assembly control block 180 directs the overall operation of the sensor assembly. Sensor assembly control block 180 first asserts a flow control signal 190 to pump 152. The flow control signal 190 is shown explicitly in FIG. 8. In response, pump 152 draws a sample from flue 182 and provides the sample, at a desired pressure, to preheater 154 and eventually to channel 158. Preheater 154 preheats and the heater maintains the sample gas at optimal operating element temperature and thus helps to prevent loss of sample due to condensation and to increase the amount of constituents that can be accumulated in each of the interactive elements.

The sample fluid stream passes down channel 158 for a predetermined time period 192 until the interactive elements reach a state of substantially saturation of adsorption of one or more constituents from the sample fluid stream and reach equilibrium. Thereafter, the sensor assembly control block 180 notifies heater control block 166 to begin heating the heater elements in a time phased sequence. The heater control block 166 first provides a first heater enable signal 194 and a separation heater enable signal 196, as better shown in FIG. 8. The first heater enable signal 194 turns on transistor 168a, and the separation heater enable signal 196 turns on transistor 170. Transistor 168a provides current to the first heater element 160a, causing the first heater element 160a to increase in temperature. This heats the corresponding interactive element, which desorbs one or more constituents into the sample fluid stream in the form of a first concentration pulse. The first concentration pulse is carried downstream toward the second heater element 160b by the sample fluid stream. This process is repeated for the 3rd, 4th and N-th element as follows:

The heater control block 166 then provides a second heater enable signal 198, which turns on transistor 168b. Transistor 168b provides current to the second heater element 160b, causing the second heater element 160b to increase in temperature. This heats the corresponding interactive element, which desorbs one or more constituents into the sample fluid stream in the form of a second concentration pulse. Preferably, the heater control block 166 times the second heater enable signal 198 such that the second concentration pulse substantially overlaps the first concentration pulse. Both the first and second concentration pulses are carried downstream toward the third heater element 160c.

The timing of the second heater enable signal 198 relative to the first heater enable signal 194 may be established by prior calibration. More preferably, however, the heater control block 166 senses the resistance of the second heater element 160b. It is recognized that the resistance of the second heater element 160b will begin to change when the first concentration pulse arrives at the second heater element 160b because the first concentration pulse is typically hotter than the sample fluid stream. Once a predetermined resistance change is sensed in the second heater element 160b, the heater control block 166 may energize the second heater element 160b via transistor 168b. The remaining heater enable signals may be likewise controlled.

The heater control block 166 then provides a third heater enable signal 200, which turns on transistors 168c. Transistor 168c provides current to the third heater element 160c, causing the third heater element 160c to increase in temperature. This heats the corresponding interactive element, which desorbs one or more constituents into the sample fluid stream in the from of a third concentration pulse. Preferably, the heater control block 166 t times the third heater enable signal 200 such that the third concentration pulse substantially overlaps the first and second concentration pulses. The first, second, and third substantially overlapping concentration pulses are carried downstream toward the "Nth" heater element 160d.

The heater control block 166 then provides ant "Nth" heater enable signal 202, which turns on transistors 168c. Transistor 168c provides current to the "Nth" heater element 160d, causing the "Nth" heater element 160d to increase in temperature. This heats the corresponding interactive element, which desorbs one or more constituents into the sample fluid stream in the form of an "Nth" concentration pulse. Preferably, the heater control block 166 times the "Nth" heater enable signal 202 such that the "Nth" concentration pulse substantially overlaps the previously generated concentration pulses. The resulting concentration pulse is carried downstream to the separator heater 162. The separator heater, in conjunction with the channel 158, separates selected constituents in the concentration pulse into individual constituent components. The individual constituent components may include one or more compounds, depending on a number of factors including the sample gas provided.

Transistor 170 then energizes the separation heater 162, which separates the various constituents into individual components, as described above. The separated constituents are carried downstream to detector 164 by the sample fluid stream. The detector 164 may be a thermal conductivity detector, discharge ionization detector, or any other type of detector such as those commonly used in gas chromatography. The detector 164 preferably senses the concentration levels of each individual constituent component, and provides a corresponding signal to amplifier 210. Amplifier 210 amplifies the detector output signal and preferably provides the detector output signal to a data processing unit for analysis. It is contemplated that the heater control block 166 may provide a detector enable signal 212 to enable the detector only when the individual constituent components are present.

Figure 9:
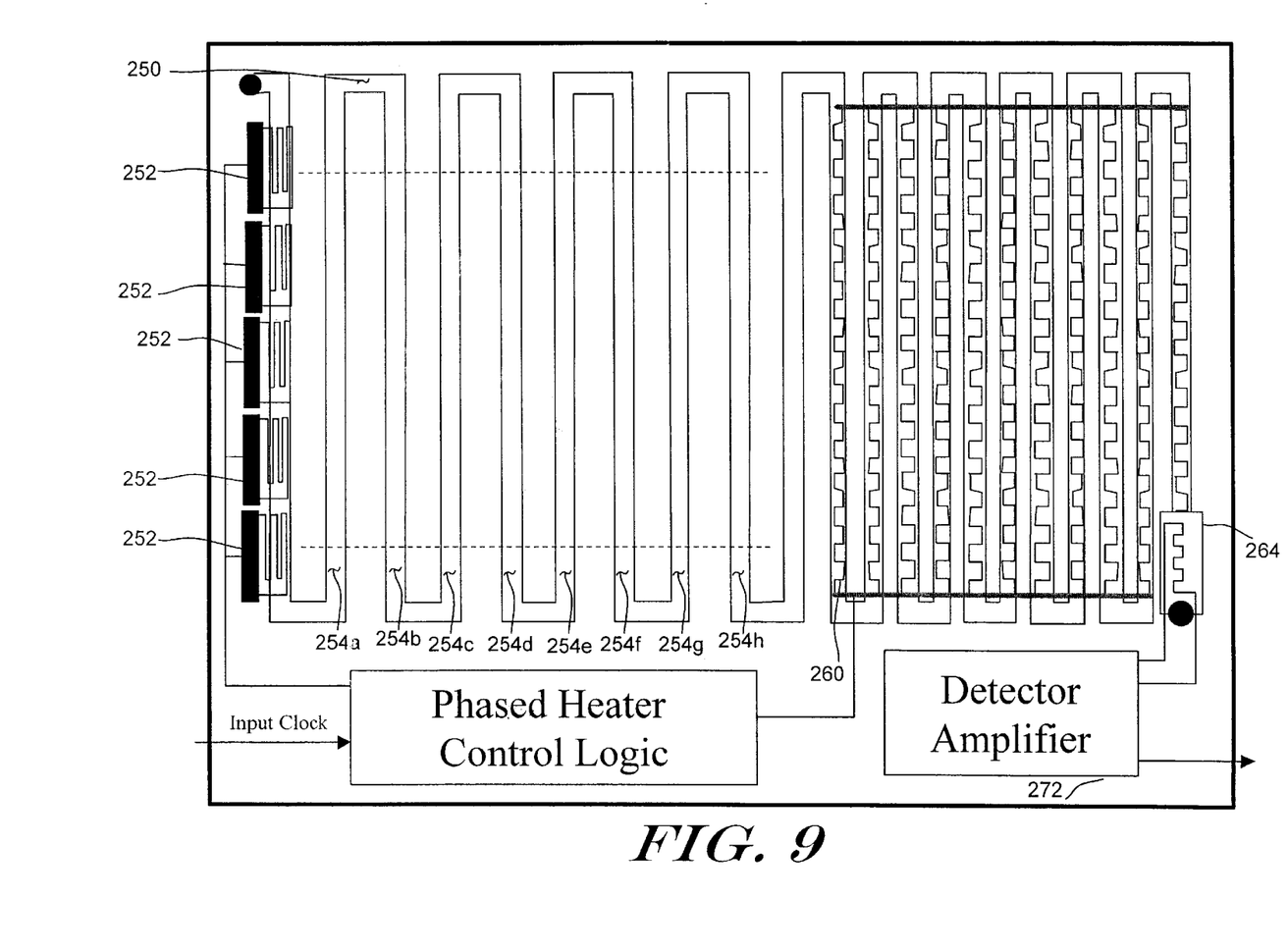
FIG. 9 is a simplified layout of an integrated circuit that includes a concentrator, a separator, and a sensor in accordance with the present invention.

FIG. 9 is a simplified layout of an integrated circuit that includes a concentrator, a separator, and a detector in accordance with the present invention. The integrated circuit preferably includes a channel 250 that traverses back and forth across the chip. A first part of the channel 250 has a number of heater elements 252 extending thereover on a support member, as described above. Interactive elements (not explicitly shown) are positioned in the channel 250 adjacent each of the heater elements. While only one column of heater elements 252 is shown, it is contemplated that each of the channel legs 254a–h may have a column of heater elements 252. In a preferred embodiment, there are between one hundred and one thousand heater elements spaced along channel 250.

A second downstream portion of the channel 250 has a separation heater 260 extending thereover. The separation heater helps separate the various constituents in the concentration pulses provided by the heater elements 252. Finally, a detector 264 is provided over the channel 250 downstream of the separation heater 260. The detector preferably senses the concentration of each of the separated constituent components provided by the separator.

Because the concentrator, separator, and detector are provided on an integrated circuit, other conventional electronic circuits can be easily integrated therewith. In the embodiment shown, a phased heater control block 270 and amplifier 272 are fabricated on the same substrate. Chemical sensors, especially chemical microsensors as described, potentially afford many attractive features such as low cost, high sensitivity, ruggedness, and (in the case of microsensors) small size.

Having thus described the preferred embodiments of the present invention, those of skill in the art will readily appreciate that the teachings found herein may be applied to yet other embodiments within the scope of the claims hereto attached.

What is claimed is:

1. A concentrator for concentrating one or more constituents of a sample fluid stream, comprising:
    two or more interactive elements spaced along and exposed to the sample fluid stream, each of the interactive elements include an interactive substance that adsorbs and desorbs selected constituents of the sample fluid stream depending on the temperature of the interactive element, wherein at least two of the interactive elements include the same interactive substance;
    two or more heater elements, each heater element in thermal communication with a corresponding interactive element; and
    controller means coupled to the two or more heater elements for allowing the two or more interactive elements to become exposed to the sample fluid stream before energizing the heater elements in a time phased sequence.

2. A concentrator according to claim 1, wherein the two or more interactive elements comprise different portions of an interactive layer exposed to and extending along at least part of the sample fluid stream.

3. A concentrator according to claim 2, wherein each of the two or more heater elements are in thermal communication with a corresponding portion of the interactive layer.

4. A concentrator according to claim 1, wherein the interactive elements are of equal length.

5. A concentrator according to claim 1, wherein the interactive substance is a silica gel.

6. A concentrator according to claim 1, wherein the interactive substance is an active carbon.

7. A concentrator for concentrating one or more constituents of a sample fluid stream, comprising:
    two or more interactive elements spaced along and exposed to the sample fluid stream, each of the interactive elements include an interactive substance that adsorbs and desorbs selected constituents of the sample fluid stream depending on the temperature of the interactive element;
    two or more heater elements, each heater element in thermal communication with a corresponding interactive element; and
    controller means coupled to the two or more heater elements for allowing the two or more interactive elements to become exposed to the sample fluid stream before energizing the heater elements in a time phased sequence, said controller means including first energizing means for energizing a first heater element, second energizing means for energizing a second heater element that is located downstream of the first heater element, and a controller for activating said first energizing means, which causes the corresponding interactive element to become heated and desorb selected constituents into the sample fluid stream which produces a first concentration pulse that is carried by the sample fluid stream downstream toward the second heater element, and for activating said second energizing means when the first concentration pulse reaches the second heater element.

8. A concentrator according to claim 7, wherein the first heater element and the second heater element include a resistive material.

9. A concentrator according to claim 8, wherein said first energizing means energizes said first heater clement by providing a first voltage, currents, or power pulse, and said second energizing means energizes said second heater element by providing a second voltage, current, or power pulse.

10. A concentrator for concentrating one or more constituents of a sample fluid stream, comprising:
    two or more interactive elements spaced along and exposed to the sample fluid stream, each of the interactive elements include an interactive substance that adsorbs and desorbs selected constituents of the sample fluid stream depending on the temperature of the interactive element;
    two or more heater elements, each heater element in thermal communication with a corresponding interactive element; and
    controller means coupled to the two or more heater elements for energizing the heater elements in a time phased sequence, said controller means including first energizing means for energizing a first heater element with a first energy pulse, second energizing means for energizing a second heater element that is located downstream of the first heater element with a second energy pulse, and a controller for activating said first energizing means, which causes the corresponding interactive element to become heated and desorb selected constituents into the sample fluid stream which produces a first concentration pulse that is carried by the sample fluid stream downstream toward the second heater element, and for activating said second energizing means when the first concentration pulse reaches the second heater element, wherein the first energy pulse and the second energy pulse result in triangular shaped temperature pulses of the adsorption layer.

11. A concentrator for concentrating one or more constituents of a sample fluid stream, comprising:
    two or more interactive elements spaced along and exposed to the sample fluid stream, each of the interactive elements include an interactive substance that adsorbs and desorbs selected constituents of the sample fluid stream depending on the temperature of the interactive element;
    two or more heater elements, each heater element in thermal communication with a corresponding interactive element; and
    controller means coupled to the two or more heater elements for energizing the heater elements in a time phased sequence, said controller means including first energizing means for energizing a first heater element with a first energy pulse, second energizing means for energizing a second heater element that is located downstream of the first heater element with a second energy pulse, and a controller for activating said first energizing means, which causes the corresponding interactive element to become heated and desorb selected constituents into the sample fluid stream which produces a first concentration pulse that is carried by the sample fluid stream downstream toward the second heater element, and for activating said second energizing means when the first concentration pulse reaches the second heater element, wherein the first energy pulse and the second energy pulse result in square shape temperature pulses of the adsorption layer.

12. A concentrator for concentrating one or more constituents of a sample fluid stream, comprising:

two or more interactive elements spaced along and exposed to the sample fluid stream, each of the interactive elements include an interactive substance that adsorbs and desorbs selected constituents of the sample fluid stream depending on the temperature of the interactive element;

two or more heater elements, each heater element in thermal communication with a corresponding interactive element; and controller means coupled to the two or more heater elements for energizing the heater elements in a time phased sequence, said controller means including first energizing means for energizing a first heater element with a first energy pulse, second energizing means for energizing a second heater element that is located downstream of the first heater element with a second energy pulse, and a controller for activating said first energizing means, which causes the corresponding interactive element to become heated and desorb selected constituents into the sample fluid stream which produces a first concentration pulse that is carried by the sample fluid stream downstream toward the second heater element, and for activating said second energizing means when the first concentration pulse reaches the second heater element, wherein the first energy pulse and the second energy pulse result in bell shaped temperature pulses of the adsorption layer.

13. A concentrator for concentrating one or more constituents of a sample fluid stream, comprising:

two or more interactive elements spaced along and exposed to the sample fluid stream, wherein each of the interactive elements includes an interactive substance that adsorbs and desorbs selected constituents of the sample fluid stream depending on the temperature of the interactive element wherein each of the interactive elements has a length that is greater than the length of each interactive clement located further upstream in the sample fluid stream;

two or more heater elements, each heater element in thermal communication with a corresponding interactive element; and controller means coupled to the two or more heater elements for energizing the heater elements in a time phased sequence.

14. A sensor assembly for sensing the enhanced concentration of one or more constituents in a sample fluid stream, comprising:

two or more interactive elements spaced along and exposed to the sample fluid stream, each of the interactive elements include an interactive substance that adsorbs and desorbs selected constituents of the sample fluid stream depending on the temperature of the interactive element;

two or more heater elements, each heater element in thermal communication with a corresponding interactive element;

controller means coupled to the two or more heater elements for allowing the two or more interactive elements to become exposed to the sample fluid stream before energizing the heater elements in a time phased sequence such that each of the interactive elements becomes heated and desorbs selected constituents into the sample fluid stream at substantially the time that an upstream concentration pulse, produced by one or more upstream interactive elements, reaches the interactive element;

separator means for separating selected constituents of one of the concentration pulses provided by one or more of the interactive elements into individual constituent components; and detector means for sensing the concentration of one or more of the individual constituent components.

15. A sensor assembly according to claim 14, wherein said detector means includes a thermal conductivity detector.

16. A sensor assembly according to claim 14, further comprising a pump for providing the sample fluid stream.

17. A sensor assembly according to claim 14, wherein the sample fluid stream is driven by thermal convection.

18. A sensor assembly according to claim 14, further includes a preheater for preheating at least a portion of the sample fluid stream.

19. A sensor assembly according to claim 18, wherein said preheater heats the sample fluid stream throughout the sensor assembly.

20. A sensor assembly according to claim 18, wherein said preheater heats the sample fluid stream only in the separation means.

21. A sensor assembly according to claim 14, further includes a cooler for cooling at least a portion of the sample fluid stream.

22. A method for concentrating one or more constituents of a sample fluid stream, the method comprising the steps of:

providing two or more interactive elements spaced along and exposed to the sample fluid stream, each of the interactive elements include an interactive substance that adsorbs and desorbs selected constituents of the sample fluid stream depending on the temperature of the interactive clement, where at least two of the interactive elements include the same interactive substance;

waiting for the interactive substance to adsorb one or more constituents from the sample fluid stream; and heating the two or more interactive elements in a time phased sequence.

23. A method for concentrating one or more constituents of a sample fluid stream, the method comprising the steps of:

providing two or more interactive elements spaced along and exposed to the sample fluid stream, each of the interactive elements include an interactive substance that adsorbs and desorbs selected constituents of the sample fluid stream depending on the temperature of the interactive element, where at least two of the interactive elements incorporate the same interactive substance;

waiting for the interactive substance to adsorb one or more constituents from the sample fluid stream; and heating the two or more interactive elements in a time phased sequence, wherein said heating step includes the steps of:

heating an upstream interactive element, which causes the upstream interactive element to desorb selected constituents into the sample fluid stream to produce a first concentration pulse that is carried by the sample fluid stream downstream toward a downstream interactive element; and heating the downstream interactive element when the first concentration pulse reaches the downstream interactive element, which causes the downstream interactive element to desorb selected constituents into the sample fluid stream and at least partially overlap the first concentration pulse to produce a second concentration pulse that is carried by the sample fluid stream downstream.

24. A method for concentrating one or more constituents of a sample fluid stream, the method comprising the steps of:

providing N interactive elements, where N is greater than one, each of the N interactive elements being spaced along and exposed to the sample fluid stream, each of the N interactive elements including an interactive substance that adsorbs and desorbs selected constituents of the sample fluid stream depending on the temperature of the interactive element such that, when heated, each of the N interactive elements desorb selected constituents into the sample fluid stream to produce a corresponding concentration pulse that is carried by the sample fluid stream downstream toward a downstream interactive element;

exposing the N interactive elements to the sample fluid stream;

waiting for the N interactive elements to adsorb one or more constituents from the sample fluid stream; and heating the N interactive elements in a time phased sequence whereby each of the downstream interactive elements is heated when the concentration pulse provided by one or more of the upstream interactive elements reaches the downstream interactive element.

25. A method according to claim 24, further comprising the step of sensing the concentration of selected constituents present in the concentration pulse provided by one or more of the N interactive elements.

26. A method according to claim 25, further comprising the step of separating selected constituents of the concentration pulse provided by one or more of the N interactive elements into individual components.

27. A method according to claim 26, further comprising the step of sensing the concentration of one or more of the individual components.

28. A method for concentrating one or more constituents of a sample fluid stream that is flowing through a channel having an interactive substance provided therein, the interactive substance adsorbing and desorbing selected constituents of the sample fluid stream depending on the temperature of the interactive substance, the interactive substance having an upstream portion and a downstream portion, the method comprising the steps of:

waiting for the interactive substance to adsorb one or more constituents from the sample fluid stream;

heating the upstream portion of the interactive substance, causing the upstream portion to desorb selected constituents into the sample fluid stream to produce a first concentration pulse, the first concentration pulse is carried by the sample fluid stream downstream toward the downstream portion of the interactive substance; and heating the downstream portion of the interactive substance when the first concentration pulse reaches the downstream portion, causing the downstream portion of the interactive substance to desorb selected constituents into the sample fluid stream and at least partially overlap the first concentration pulse to produce a second concentration pulse that is carried by the sample fluid stream downstream.

29. A concentrator for concentrating one or more constituents of a sample fluid stream, comprising:

two or more interactive elements spaced along and exposed to the sample fluid stream, each of the interactive elements include an interactive substance that adsorbs and desorbs selected constituents of the sample fluid stream depending on the temperature of the interactive element, wherein at least two of the interactive elements are disposed within the sample fluid stream such that the sample fluid must pass by a first interactive element and then a second interactive element;

two or more heater elements, each heater element in thermal communication with a corresponding interactive e element; and controller means coupled to the two or more heater elements for allowing the two or more interactive elements to become exposed to the sample fluid stream before energizing the heater elements in a time phased sequence.

\* \* \* \* \*